US005696168A

United States Patent [19]
Heiligenstein et al.

[11] Patent Number: 5,696,168
[45] Date of Patent: Dec. 9, 1997

[54] TREATMENT OF ATTENTION-DEFICIT/ HYPERACTIVITY DISORDER

[75] Inventors: John Harrison Heiligenstein; Bennett Coleman Laguzza, both of Indianapolis; Steven Marc Paul, Carmel; Gary Dennis Tollefson, Indianapolis, all of Ind.

[73] Assignee: Eli Lilly and Company, Indianapolis, Ind.

[21] Appl. No.: 682,040

[22] Filed: Jul. 16, 1996

[51] Int. Cl.$^6$ .................................................. A61K 31/135
[52] U.S. Cl. ......................................................... 514/649
[58] Field of Search ................................... 514/438, 649

[56] References Cited

U.S. PATENT DOCUMENTS 4,956,388  9/1990  Robertson et al. ..................... 514/651

FOREIGN PATENT DOCUMENTS

93/0694  7/1993  South Africa .

OTHER PUBLICATIONS

Green, Wayne H., *Child Adolesc. Psychi. Clinics North America*, 1, 449–465 (1992).
Spencer, et al., *J. Am. Acad. Child Adolesc. Psychiatry*, 32, 205–210 (1993).
Biederman, et al., *J. Am. Acad. Child Adolesc. Psychiatry*, 28, 777–784 (1989).
Wilens, et al., *J. Am. Acad. Child Adolesc. Psychiatry*, 32, 343–349 (1993).
Biederman, et al., *Am. J. Psychiatry*, 148, 564–577.
Biederman, et al., *Am. J. Psychiatry*, 150, 1792–1798 (1993).
Gehlert, et al., *Neuroscience Ltrs.*, 157, 203–206 (1993).
Wong, et al., *J. Pharmacol. Exp. Therap.*, 222, 61–65 (1982).
Wong, David T., and Bymaster, Frank P., *Research Comm. Chem. Pathol. Pharmacol.*, 15, 221–231 (1976).
Fuller, Ray W., and Wong, David T., *J. Clin. Psychopharmacol.*, 7, 6 Suppl., 36S–43S (1987).
Wong, et al., *Neuropsychopharmacology*, 8, 23–33 (1993).
Fuller, et al., *J. Pharmacol. Exp. Ther.*, 269, 132–136 (1994).
Ikeda, et al., *Neuropsychopharmacology*, 10, Suppl. Pt. 1, 650S (1994).
Zerbe, et al., *J. Pharmacol. Exp. Ther.*, 232, 139–143 (1985).
Chumpradit, et al., *J. Med. Chem.*, 35, 4492–4497 (1992).
Oberlender, et al., *J. Pharm. Pharmacol.*, 39, 1055–1056 (1987).
Steinberg, et al., *Am. J. Psychiatry*, 142, 1517–1518 (1985).
Chouinard, et al., *Psychopharmacology*, 83, 126–128 (1984).
Chouinard, et al., *Psychopharmacol. Bull.*, 21, 73–76 (1985).
Farid, et al., *J. Clin. Pharmacol.*, 25, 296–301 (1985).
Fuller, et al., *Res. Comm. Chem. Pathol. Pharmacol.*, 41, 169–172 (1983).

Zhang, et al., *J. Pharmacol. Exp. Ther.*, 259, 1088–1093 (1991).
Springer, et al., *J. Urology*, 152, 515–519 (1994).
Terry, et al., *J. Pharmacol. Exp. Ther.*, 270, 1041–1048 (1994).
Johanson, et al., *J. Pharmacol. Exp. Ther.*, 267, 1–8 (1993).
Keshavarzian, et al., *Gastroenterology*, 98, 554–560 (1990).
Cusack, et al., *Psychopharmacology*, 114, 559–565 (1994).
Ryan, Neal D., *J. Child Adolesc. Psychopharmacol.*, 1, 21–31 (1990).
"Imipramine", *Physicians' Desk Ref.*, 1070–1074 (1993).
"Desipramine", *Physicians' Desk Ref.*, 1389–1390 (1993).
"Nortriptyline", *Physicians' Desk Ref.*, 2115–2116 (1993).
"Amitriptyline", *Physicians' Desk Ref.*, 2372–2374 (1993).
"Clomipramine", *Physicians' Desk Ref.*, 671–675 (1993).
"Bupropion", *Physicians' Desk Ref.*, 842–844 (1993).
"Fluoxetine", *Physicians' Desk Ref.*, 877–880 (1994).
"Chlorpromazine", *Physicians' Desk Ref.*, 2327–2330 (1993).
"Clonidine", *Physicians' Desk Ref.*, 612–614 (1994).
*The Medical Letter*, 32, p. 53, Jun. 1990.
Riddle, et al., *J. Am. Acad. Child Adolesc. Psychiatry*, 30; 1, 104–108 (1991).
Geller, Barbara, *J. Am. Acad. Child Adolesc. Psychiatry*, 30:4, 682–684 (1991).
Wilens, et al., *J. Am. Acad. Child Adolesc. Psychiatry*, 31:4, 691–698 (1992).
Biederman, et al., *J. Am. Acad. Child Adolesc. Psychiatry*, 32:4, 805–813 (1993).
Walsh, et al., *J. Am. Acad. Child Adolesc. Psychiatry*, 33:2, 191–197 (1994).
"Letters to the Editor", *J. Am. Acad. Child Adolesc. Psychiatry*, 33:4, 588–590 (1994).
"Letters to the Editor", *J. Am. Acad. Child Adolesc. Psychiatry*, 34:2, 125–126 (1995).
Werry, John S., *J. Am. Acad. Child Adolesc. Psychiatry*, 34:9, 1239–1248 (1995).
Leonard, et al., *J. Am. Acad. Child Adolesc. Psychiatry*, 34:11, 1460–1468 (1995).
Rudorfer, et al., *J. Clin. Psychopharmacol.*, 11, 22–27 (1991).
Delgado, et al., *Psychopharm. Bull.*, 29, 389–396 (1993).
Asnis, et al., *Am. J. Psychiatry*, 152, 31–36 (1995).
Delgado, et al., *Arch. Gen. Psychiatry*, 51, 865–874 (1994).
Benkert, et al., *International Clin. Psychopharma.*, 8 Suppl. 1, 3–14 (1993).
Hudson, et al., *Am. J. Psychiatry*, 147, 552–564 (1990).
Kihara, et al., *J. Pharmacol. Exp. Ther.*, 272, 177–183 (1995).
Wong, D.T., and Shaw, W.N., *Soc. Neuroscience Abstracts*, 19, 1239 (1993).
Murphy, et al., *Soc. Neuroscience Abstracts*, 15, 58 (1989).

*Primary Examiner*—Kimberly Jordan
*Attorney, Agent, or Firm*—Robert D. Titus; David E. Boone

[57] ABSTRACT

A group of propanamines, norepinephrine uptake inhibitors, are used to treat attention-deficit/hyperactivity disorder.

14 Claims, No Drawings

TREATMENT OF ATTENTION-DEFICIT/HYPERACTIVITY DISORDER

This application claims the benefit of U.S. Provisional Application No. 60/001,373, filed Jul. 24, 1995, and U.S. Provisional Application No. 60/006,349, filed Nov. 8, 1995.

FIELD OF THE INVENTION

The invention belongs to the fields of pharmaceutical chemistry and psychiatric medicine, and provides a method of treatment of the psychiatric disorder known as attention-deficit/hyperactivity disorder.

BACKGROUND OF THE INVENTION

For some decades it has been recognized that a significant number of children are persistently hyperactive and have an attention span so short as to be disabling in school and in many personal relationships. Such children in earlier times would no doubt have been dismissed as incorrigible and punished or even confined in an institution. Some long time ago, however, it was realized that these children cannot control their hyperactivity and inattention, and the medical professions began to try to help them. Methylphenidate (Ritalin™) has been used for some time to treat such children and it often significantly improves their ability to function and coexist with other people at school and at home. However, the drug has the disadvantages of requiring several doses per day, and producing a rebound effect as the effect of each dose fades away. Further, the drug causes sleeplessness and lack of appetite in some patients. Methylphenidate has both noradrenergic and dopaminergic activities.

Imipramine, desipramine, nortriptyline, amitriptyline and clomipramine are also used in some cases of attention-deficit/hyperactivity disorder (ADHD). Those tricyclic drugs, however, have a number of physiological mechanisms and, as a class, tend to produce a number of side effects and require careful supervision and dose titration.

In the last decade, psychiatrists have realized that ADHD is not only a disorder of childhood, but often continues in the adult. It is obvious that hyperactivity and short attention span cause grave disruption in an adult's life, but it is only recently that such patients have been able to obtain any treatment.

The need for a safe and convenient treatment for ADHD, applicable to both children and adults and without the disadvantages possessed by methylphenidate continues to be a concern of the psychiatric profession.

SUMMARY OF THE INVENTION

The present invention provides a method of treating attention-deficit/hyperactivity disorder comprising the administration to a patient in need of such treatment of an effective amount of duloxetine, or of a compound of the formula

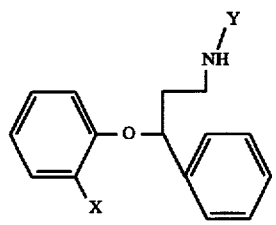

wherein $X=C_1-C_4$ alkylthio, and $Y=C_1-C_2$ alkyl or a stereoisomer thereof, or a pharmaceutically acceptable salt thereof.

DETAILED DESCRIPTION

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

The compounds of formula I were described in U.S. Pat. No. 5,281,624, of Gehlert, Robertson and Wong, and in Gehlert, et al., *Life Sciences*, 56(22), 1915–1920, 1995. The compounds are there taught to be inhibitors of norepinephrine reuptake in the brain. It is also explained that the compounds exist as stereoisomers, and that they accordingly include not only the racemates, but also the isolated individual isomers. For example, the compounds of formula I include the following exemplary species.

N-ethyl-3-phenyl-3-(2-methylthiophenoxy) propylamine benzoate (R)-N-methyl-3-phenyl-3-(2-propylthiophenoxy) propylamine hydrochloride (S)-N-ethyl-3-phenyl-3-(2-butylthiophenoxy) propylamine N-methyl-3-phenyl-3-(2-ethylthiophenoxy) propylamine malonate (S)-N-methyl-3-phenyl-3-(2-t-butylthiophenoxy) propylamine naphthalene-2-sulfonate (R)-N-methyl-3-(2-methylthiophenoxy)-3-phenylpropylamine (S)-N-methyl-3-phenyl-3-(2-t-butylthiophenoxy) propylamine naphthalene-2-sulfonate The compounds used in this invention are safe drugs, and their use in ADHD, in both adults and children, is a superior treatment for that disorder because of their improved safety. The compounds are particularly selective, having few if any physiological effects besides that on norepinephrine processing, and therefore are free of side effects and unwanted activities. Further, they are effective at relatively low doses, as discussed below, and may safely and effectively be administered once per day. Thus, difficulties created by the multiple dosing of patients, who are children and disorganized adults, are completely avoided.

The present invention is described as a method of treating ADHD. It is not intended, of course, that every use of the invention will result in a complete cure of the disorder. Treatment of psychiatric disorders is not that precise. It is intended, however, that the use of the invention will result in improvement of the treated ADHD patient which will approach complete cure in some cases. In other cases, a lesser degree of improvement, still benefiting the patient, will be obtained. Such treatment is carried out by administering an effective amount of the chosen compound. It will be understood that amount is an amount which produces treatment of the patient at hand.

The effective dose of a compound of this invention for ADHD is in the range from about 1 mg/day to about 100 mg/day. The preferred adult dose is in the range from about 5 to about 80 mg/day, and a more highly preferred adult dose is from about 10 to about 60 mg/day. The children's dose of course is smaller, in the range from about 1 to about 70 mg/day, more preferably from about 5 to about 60 mg/day and still more preferably from about 5 to about 50 mg/day. The optimum dose for each patient, as always, must be set by the physician in charge of the case, taking into account the patient's size, other medications which the patient requires, severity of the disorder and all of the other circumstances of the patient.

Since the compounds are readily orally absorbed and require only once/day administration, there is little or no reason to administer them in any other way than orally. They may be produced in the form of a clean, stable crystal, and thus are easily formulated in the usual oral pharmaceutical forms, such as tablets, capsules, suspensions, and the like. The usual methods of pharmaceutical scientists are applicable. They may usefully be administered, if there is any reason to do so in a particular circumstance, in other pharmaceutical forms, such as injectable solutions, depot injections, suppositories and the like, which are well known to and understood by pharmaceutical scientists. It will substantially always be preferred, however, to administer a compound as a tablet or capsule and such pharmaceutical forms are recommended.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

Example

| 10 mg Duloxetine base/capsule | |
|---|---|
| Bill of Materials | |
| Beads | |
| Sucrose - starch nonpareils, 20-25 mesh | 60.28 mg |
| Duloxetine layer | |
| Duloxetine | 11.21 |
| Hydroxypropylmethylcellulose | 3.74 |
| Separating layer | |
| Hydroxypropylmethylcellulose | 2.51 |
| Sucrose | 5.00 |
| Talc, 500 mesh | 10.03 |
| Enteric layer | |
| HPMCAS, LF grade, Shin-Etsu Chemical Co., Tokyo, Japan | 25.05 |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60 mg |

The duloxetine layer was built up by suspending duloxetine in a 4% w/w solution of the hydroxypropylmethylcellulose in water, and milling the suspension with a CoBall Mill (Fryma Mashinen AG, Rheinfelden, Switzerland) model MS-12. A fluid bed dryer with a Wurster column was used to make this product, at a batch size of 1.0 kg. The separating layer was added from a 4% w/w solution of the hydroxypropylmethylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/ hydroxypropylmethylcellulose solution containing titanium dioxide and propylene glycol as plasticizer. The pellets were completely dried in the fluid bed dryer and then were then filled in size 3 gelatin capsules.

The ADHD patient is rather readily recognized, and most people have been in contact with children, if not adults, who exhibit some or all of the symptoms of the disorder. The best description of the disorder is the diagnostic criteria for ADHD, published by the American Psychiatric Association in the Diagnostic and Statistical Manual of Mental Disorders, Fourth Version (1994), as follows.

Diagnostic criteria for Attention-Deficit/ Hyperactivity Disorder

A. Either (1) or (2):
  (1) six (or more) of the following symptoms of inattention have persisted for at least 6 months to a degree that is maladaptive and inconsistent with developmental level: Inattention
    (a) often fails to give close attention to details or makes careless mistakes in schoolwork, work, or other activities
    (b) often has difficulty sustaining attention in tasks or play activities
    (c) often does not seem to listen when spoken to directly
    (d) often does not follow through on instructions and fails to finish schoolwork, chores, or duties in the workplace (not due to oppositional behavior or failure to understand instructions)
    (e) often has difficulty organizing tasks and activities
    (f) often avoids, dislikes, or is reluctant to engage in tasks that require sustained mental effort (such as schoolwork or homework)
    (g) often loses things necessary for tasks or activities (e.g., toys, school assignments, pencils, books, or tools)
    (h) is often easily distracted by extraneous stimuli
    (i) is often forgetful in daily activities
  (2) six (or more) of the following symptoms of hyperactivity-impulsivity have persisted for at least 6 months to a degree that is maladaptive and inconsistent with developmental level:

Hyperactivity
(a) often fidgets with hands or feet or squirms in seat
(b) often leaves seat in classroom or in other situations in which remaining seated is expected
(c) often runs about or climbs excessively in situations in which it is inappropriate (in adolescents or adults, may be limited to subjective feelings of restlessness)
(d) often has difficulty playing or engaging in leisure activities quietly
(e) is often "on the go" or often acts as if "driven by a motor"
(f) often talks excessively Impulsivity
(g) often blurts out answers before questions have been completed
(h) often has difficulty awaiting turn
(i) often interrupts or intrudes on others (e.g., butts into conversations or games)

B. Some hyperactive-impulsive or inattentive symptoms that caused impairment were present before age 7 years.
C. Some impairment from the symptoms is present in two or more settings (e.g., at school [or work] and at home).
D. There must be clear evidence of clinically significant impairment in social, academic, or occupational functioning.
E. The symptoms do not occur exclusively during the course of a Pervasive Developmental Disorder, Schizophrenia, or other Psychotic Disorder and are not better accounted for by another mental disorder (e.g., Mood Disorder, Anxiety Disorder, Dissociative Disorder, or a Personality Disorder).

It will be seen that ADHD is a disorder made up of two components, the attention deficit component and the hyperactivity component, which are to a degree independent. Treatment with the compounds is effective in patients who are primarily suffering from either component or from the combined disorder.

While ADHD is still primarily regarded as a disorder of children, it is now understood that many ADHD patients, as many as 50%, continue to suffer from the disorder as they grow through adolescence into adulthood. Biederman and associates have extensively studied the adult ADHD patient, and have found numerous cases. See, for example, Biederman, et al., Am. J. Psychiatry 150, 1792–98 (1993). They found that cases of adult ADHD were frequently found among the parents and adult siblings of childhood ADHD patients. Thus, it appears that the disease is not only carried forward into adulthood, but is inheritable.

The Biederman, et al. article cited immediately above, as well as another article by the same authors, Am. J. Psychiatry 148, 564–77 (1991), reports studies of ADHD patients who also have one or more other psychiatric disorders. The authors indicate that such psychiatric co-morbidity is quite common among ADHD patients and, naturally, cloud the diagnosis and treatment of such patients. The compounds are effective in the treatment of ADHD, even though the situation of the treated patient may be complicated by co-morbidity with one or more additional disorders.

The mere listing of the above diagnostic criteria indicates the seriousness of ADHD and the damage which it does to the patient. A person having a moderately severe case of ADHD is substantially entirely unable to concentrate and hence unable to do meaningful work or study; is a continuing distraction and nuisance to those around her or him, because of the uselessly impulsive activity which the disorder causes; and consumes his or her family in cleaning up and repairing the damage and disruption which he or she causes. Such a patient of school age may substantially damage the teacher's ability to accomplish the class' goals, because the ADHD child will continually disrupt the class, distract the other children and consume the teacher's effort. Thus, it is readily apparent that an improved treatment of ADHD is needed, and that the present invention is accordingly important to many people.

The method of the present invention is effective in the treatment of patients who are children, adolescents or adults, and there is no significant difference in the symptoms or the details of the manner of treatment among patients of different ages. In general terms, however, for purposes of the present invention, a child is considered to be a patient below the age of puberty, an adolescent is considered to be a patient from the age of puberty up to about 18 years of age, and an adult is considered to be a patient of 18 years or older.

We claim:

1. A method of treating attention-deficit/hyperactivity disorder comprising administering to a patient in need of such treatment an effective amount of a compound of the formula

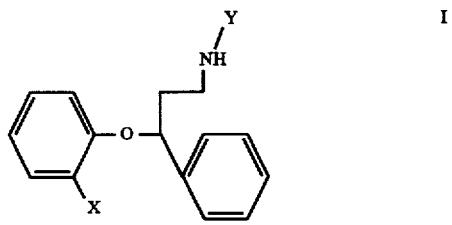

wherein $X=C_1-C_4$ alkylthio, and $Y=C_1-C_2$ alkyl or a stereoisomer thereof, or a pharmaceutically acceptable salt thereof.

2. A method of claim 1 wherein the compound is N-methyl-3-(2-methylthiophenoxy)-3-phenylpropylamine or a stereoisomer thereof, or a pharmaceutically acceptable salt thereof.

3. A method of claim 1 wherein the predominantly inattentive type of attention-deficit/hyperactivity disorder is treated.

4. A method of claim 1 wherein the predominantly hyperactive-impulsive type of attention-deficit/hyperactivity disorder is treated.

5. A method of claim 1 wherein the combined type of attention-deficit/hyperactivity disorder is treated.

6. A method of claim 1 wherein the patient is a child.

7. A method of claim 1 wherein the patient is an adolescent.

8. A method of claim 1 wherein the patient is an adult.

9. A method of claim 3 wherein the compound is N-methyl-3-(2-methylthiophenoxy)-3-phenylpropylamine or a stereoisomer thereof, or a pharmaceutically acceptable salt thereof.

10. A method of claim 4 wherein the compound is N-methyl-3-(2-methylthiophenoxy)-3-phenylpropylamine or a stereoisomer thereof, or a pharmaceutically acceptable salt thereof.

11. A method of claim 5 wherein the compound is N-methyl-3-(2-methylthiophenoxy)-3-phenylpropylamine or a stereoisomer thereof, or a pharmaceutically acceptable salt thereof.

12. A method of claim 9 wherein the patient is a child.

13. A method of claim 10 wherein the patient is a child.

14. A method of claim 11 wherein the patient is a child.

* * * * *